US008600493B2

(12) United States Patent
Tanner et al.

(10) Patent No.: US 8,600,493 B2
(45) Date of Patent: Dec. 3, 2013

(54) METHOD, APPARATUS AND COMPUTER PROGRAM PRODUCT FOR AUTOMATIC SEIZURE MONITORING

(75) Inventors: Antti Tanner, Espoo (FI); Mika Särkelä, Espoo (FI)

(73) Assignee: General Electric Company, Schenectady, NY (US)

( * ) Notice: Subject to any disclaimer, the term of this patent is extended or adjusted under 35 U.S.C. 154(b) by 251 days.

(21) Appl. No.: 13/190,009

(22) Filed: Jul. 25, 2011

(65) Prior Publication Data

US 2013/0030317 A1 Jan. 31, 2013

(51) Int. Cl.
*A61B 5/04* (2006.01)

(52) U.S. Cl.
USPC ........................................................ 600/544

(58) Field of Classification Search
USPC ................................................. 600/544, 545
See application file for complete search history.

(56) References Cited

U.S. PATENT DOCUMENTS 8,050,748 B2 * 11/2011 Ali et al. ....................... 600/509
2012/0071779 A1 * 3/2012 Sarkela et al. ................ 600/544

OTHER PUBLICATIONS

Pending U.S. Appl. No. 12/883,286, filed Sep. 16, 2010, entitled "Method, Apparatus and Computer Program Product for Automatic Seizure Monitoring", Sarkela et al.

"Polytopic Linear Parameter-Varying Model of Epileptiform Activity", Lu et al., 2010 American Control Conference, WeA13.4, pp. 468-473.
"Graphical Representation of Multidimensional EEG Data and Classificatory Aspects", Gasser et al., Electroencephalography and clinical Neurophysiology, 1983, 55: 609-612.
"Neural Clustering Networks based on Global Optimisation of Prototypes in Metric Spaces", Galicki et al., Neural Computing & Applications (1997) 5: 2-13.

* cited by examiner

*Primary Examiner* — Navin Natnithithadha
*Assistant Examiner* — Etsub Berhanu
(74) *Attorney, Agent, or Firm* — Andrus, Sceales, Starke & Sawall, LLP

(57) ABSTRACT

Method, apparatus and computer program product for monitoring seizure activity in brain are disclosed. At least one parameter set time series is derived from brain wave signal data obtained from a subject, wherein each parameter set sequence comprises sequential parameter sets and each parameter set comprises values for at least two signal parameters, the values being derived from the brain wave signal data. In order to reduce susceptibility to inter-subject variations and to enhance adaptability to each recording, past EEG signal data of the subject is used to determine an envelope object that encompasses the parameter points that sequential parameter sets derived from the past signal data form in a parameter space. A reference point is also determined, whose location in the parameter space depends on the past signal data. At least one new parameter point is then obtained from the subject and an evolution indicator set is determined. By examining whether the evolution indicator set fulfills predetermined location and direction criteria in relation to the envelope object and the reference point, seizure activity may be detected. The envelope object and the reference point are conditionally updated for on-line measurement.

20 Claims, 5 Drawing Sheets

METHOD, APPARATUS AND COMPUTER PROGRAM PRODUCT FOR AUTOMATIC SEIZURE MONITORING

BACKGROUND OF THE INVENTION

This disclosure relates generally to monitoring of brain wave signals. More particularly, the present invention relates to a mechanism for monitoring evolution of brain wave signals and to automatic detection of seizure activity in the brain wave signals.

About 5% of the world's population experiences seizure activity some times during their life. When seizures occur repeatedly without external stimulation, a person suffers from epilepsy. About 0.5% of the entire population belongs to that core group, which makes epilepsy the most common neurological disorder. According to the current standardization, there are two main categories of seizures: generalized and partial seizures. Generalized seizures involve the whole brain, while partial seizures involve a restricted area of the brain. The main categories are further divided to several subcategories, which describe the types of movements a person demonstrates and how the awareness and consciousness are affected during the seizure. In general, intense, paroxysmal, and involuntary muscle convulsions are called convulsions and are often related to seizures.

Electroencephalography (EEG) is a well-established method for assessing brain activity. Measurement electrodes are typically attached on the scalp to record and analyze the weak biopotential signals generated in the pyramid cells of the cortex. Alternatively, electrodes may be attached invasively between the brain and skull, or inside the brain tissue. The EEG has been in wide use for decades in basic research of the neural systems of the brain as well as in the clinical diagnosis of various central nervous system diseases and disorders.

Documentation of behavior and EEG of epileptic patients offers important information for surgery planning, diagnosis, and follow-up treatment of epilepsy. As seizures occur intermittently and unpredictably, long-term monitoring lasting for several days is typically used in order to catch enough information of the EEG and the behavioral manifestations related to seizures. These recordings are typically made in epilepsy monitoring units (EMUs) in hospitals where dedicated equipment and personnel are available for the purpose. Recent advances in the field of telemedicine and ambulatory recordings may, however, make home monitoring practicable for epileptic patients in the near future.

Long-term EEG recording produces a vast amount of EEG data, which is later reviewed by a certified specialist. In visual analysis, particular EEG waveform morphologies and dynamic patterns are searched for, which are known, based on experience, to correspond to seizures. Found morphologies and patterns are examined in detail to obtain information about the type and origin of the seizure. As the visual analysis is based on pattern recognition conducted by a human observer, the analysis process has certain limitations, such as subjectivity of seizure recognition and slowness of the analysis. Reviewing long-term EEG recordings may require several hours of work. During review, human brain may easily become exhausted and seizures may be missed, short ones in particular.

For aiding visual EEG review, automatic seizure detection algorithms have been developed since 1970s. However, because manifestation of seizure activity in EEG differs from one patient to another, development of a universally functioning automatic detector is challenging. Recent advances in the field of automatic seizure detection are related to patient-specific seizure detectors. They are closing the performance gap between a human observer and computer-based detectors. These detectors are semi-automatic; a human observer has to mark one seizure instance from the data before the detector can search for similar instances. Visual EEG review remains the state of the art of seizure detection, despite its limitations and the recent advances in computing.

Besides being important for diagnostic purposes, seizure detection has a vital role in care decisions aiming to prevent brain damage. If seizure activity does not relieve within a few minutes, the risk for irreversible brain damage increases drastically. Prolonged seizure activity is called status epilepticus (SE) and it is a major medical emergency. Patients suffering from SE are heavily treated in intensive care units (ICUs). Generalized SE leads to irreversible brain damage with lasting intellectual morbidity. Depending on the etiology, the mortality rate of generalized SE may be from 20 to 30%.

Within the last decade, the prevalence of seizures in ICU patients has been widely realized. It has been observed that even patients without a past history of epilepsy or any neurological disorder may express seizures in the ICU. The reason for these seizures may be related to critical illnesses, such as hypoxia, ischemia, intoxications, and metabolic abnormalities. Also, neurological pathologies like stroke, intracerebral hemorrhage, brain tumor, central nervous system infections, and traumatic brain injury increase the risk of seizures. What makes the seizure detection in this patient group especially challenging, is that a vast majority of the seizures are non-convulsive. That is, the patient does not exhibit intense movements during the seizure. According to the current knowledge, EEG is the only specific indicator of non-convulsive seizures. Actually, 18-34% of neurological intensive care patients suffering from unexplained depressed level of consciousness have been shown to have non-convulsive seizures and 10% of these patients are in non-convulsive status epilepticus (NCSE). According to the current understanding, non-convulsive seizures produce irreversible brain damage similarly as convulsive seizures do, and thus the medication is highly recommended for this patient group as well.

Seizure detection conducted for intensive care patients has set new requirements for automatic seizure detection algorithms. At the moment, these seizures are detected with the aid of continuous EEG monitoring and time-consuming visual EEG analysis. Seizures require acute treatment with anticonvulsants, and thus the delay related to visual reviewing is often detrimental to the patient. Consequently, there is an urgent need for automatic, on-line seizure detectors.

Commercially available automatic algorithms developed using data collected from EMUs have not been evaluated properly for ICU patient population. In EMUs, these detectors produce 0.6-2.4 false detections per hour. In the ICU environment, false positive rates are probable even higher, because the EEG of a neurologically ill ICU patient characteristically contains abnormal features closely resembling a seizure, such as triphasic waves and alpha coma. However, treating these abnormal EEG features with anticonvulsants may have detrimental effects to the patient. Therefore, reliable detection of seizure activity in the ICUs is especially important.

As described above, automatic seizure detection has been a known technical challenge for decades. Nevertheless, present-day automated seizure detection systems still have two general drawbacks: inability to adapt to a variety of different subjects and also to patient data encountered in new application areas, like the ICU. The inability to adapt to a wide variety of subjects is aggravated by the remarkable inter-individual differences in EEG seizure waveforms and by the wide dynamic variation that may occur even in the signal data of a single subject suffering from seizures. The inability to adapt to ICU patient data is aggravated by the fact that the new knowledge of the criticality of non-convulsive seizures encountered in ICU set new, more demanding criteria for the intelligence and technical performance of automatic on-line seizure detection in ICU environment.

BRIEF DESCRIPTION OF THE INVENTION

The above-mentioned problems are addressed herein which will be comprehended from the following specification. The specification describes a novel approach for monitoring a brain wave signal and detecting seizure activity through evaluation of the time evolution of the signal. In order to reduce susceptibility to inter-subject variations and to enhance adaptability to each recording, past EEG signal data of the subject is used to determine an envelope object that encompasses the parameter points that sequential parameter sets derived from the past signal data form in a parameter space. Here, a parameter point refers to the point that a set of N parameters derived from the signal channel data during one epoch defines in a parameter space whose N dimensions are defined respectively by the N parameters. Typically, N is equal to two. As the object encompasses the parameter points, it is termed envelope object in this context. Furthermore, a reference point is determined, whose location in the parameter space depends on the past signal data. The reference point may be derived from the same history data as the envelope object or from the envelope object. At least one new parameter point is then obtained from the subject and an evolution indicator set is determined that indicates the position(s) of the new point(s) in the parameter space in relation to the envelope object and the reference point. The evolution indicator set may then be employed in various ways to indicate to the user whether or not seizure activity is present. For example, if the evolution indicator set indicates that the position(s) of the new point(s) fulfill predetermined criteria with respect to the envelope object and the reference point, a decision on the presence of seizure activity may be made and the presence of seizure activity may be indicated to a user. In the opposite case, the new parameter points may be used to update the envelope object and the reference point, or at least the history data based on which the envelope object and the reference point will be calculated next time. Further, one or more evolution indicator sets may be determined based on one or more EEG channels, respectively, and the comparison results obtained from each set may be used in various ways to decide on the presence of seizure activity.

In an embodiment, a method for monitoring seizure activity in brain comprises deriving a first parameter set sequence from brain wave signal data obtained from a subject, wherein the first parameter set sequence comprises sequential parameter sets and each parameter set comprises values for at least two signal parameters, the values being derived from the brain wave signal data, and determining an envelope object from the first parameter set sequence in a parameter space defined by the at least two signal parameters, wherein the envelope object encompasses the first parameter set sequence in the parameter space. The method also comprises determining a reference point, wherein location of the reference point in the parameter space depends on the first parameter set sequence, obtaining a second parameter set sequence from the brain wave signal data, wherein the second parameter set sequence comprises at least one parameter set subsequent to the sequential parameter sets of the first parameter set sequence, and determining an evolution indicator set indicative of (a) location of the second parameter set sequence in relation to the envelope object and (b) direction of the second parameter set sequence in relation to the reference point. The method further comprises conditionally updating the envelope object and the reference point based on (i) sequential parameter sets of the first parameter set sequence and (ii) the second parameter set sequence, wherein the conditionally updating comprises performing the updating if the evolution indicator set fails to fulfill predetermined location and direction criteria indicative of seizure activity and skipping the updating if the evolution indicator set fulfills the predetermined location and direction criteria and indicating whether the evolution indicator set fulfills the predetermined location and direction criteria, thereby to produce an indication of seizure activity in the brain wave signal data.

In another embodiment, an apparatus for monitoring seizure activity in brain comprises a parameter determination unit configured to derive a first parameter set sequence from brain wave signal data obtained from a subject, wherein the first parameter set sequence comprises sequential parameter sets and each parameter set comprises values for at least two signal parameters, the values being derived from the brain wave signal data and an envelope unit configured to determine (i) an envelope object from the first parameter set sequence in a parameter space defined by the at least two signal parameters and (ii) a reference point, wherein the envelope object encompasses the first parameter set sequence in the parameter space and wherein location of the reference point in the parameter space depends on the first parameter set sequence. The apparatus also comprises an evolution indicator unit configured to define an evolution indicator set indicative of (a) location of the second parameter set sequence in relation to the envelope object and (b) direction of the second parameter set sequence in relation to the reference point, wherein the parameter determination unit is configured to derive the second parameter set sequence and wherein the second parameter set sequence comprises at least one parameter set subsequent to the sequential parameter sets of the first parameter set sequence. The apparatus further comprises an update unit configured to conditionally perform an update of the envelope object and the reference point based on (i) sequential parameter sets of the first parameter set sequence and (ii) the second parameter set sequence, wherein the update unit is configured to perform the update if the evolution indicator set fails to fulfill predetermined location and direction criteria indicative of seizure activity and skip the update if the evolution indicator set fulfills the predetermined location and direction criteria. The apparatus still comprises an indication unit configured to indicate whether the evolution indicator set fulfills the predetermined location and direction criteria, thereby to produce an indication of seizure activity in the brain wave signal data.

In a still further embodiment, a computer program product for monitoring seizure activity in brain comprises a first program product portion configured to derive a first parameter set sequence from brain wave signal data obtained from a subject, wherein the first parameter set sequence comprises sequential parameter sets and each parameter set comprises values for at least two signal parameters, the values being derived from the brain wave signal data and a second program product portion configured to determine (i) an envelope object from the first parameter set sequence in a parameter space defined by the at least two signal parameters and (ii) a reference point, wherein the envelope object encompasses the first parameter set sequence in the parameter space and wherein location of the reference point in the parameter space depends on the first parameter set sequence. The computer program product also includes a third program product portion configured to define a evolution indicator set indicative of (a) location of the second parameter set sequence in relation to the envelope object and (b) direction of the second parameter set sequence in relation to the reference point, wherein the first program product portion is configured to derive the second parameter set sequence and wherein the second parameter set sequence comprises at least one parameter set subsequent to the sequential parameter sets of the first parameter set sequence. The computer program product further comprises a fourth program product portion configured to conditionally perform an update of the envelope object and the reference point based on the (i) sequential parameter sets of the first parameter set sequence and (ii) the second parameter set sequence, wherein the fourth program product portion is configured to perform the update if the evolution indicator set fails to fulfill predetermined location and direction criteria indicative of seizure activity and skip the update if the evolution indicator set fulfills the predetermined location and direction criteria and a fifth program product portion configured to indicate whether the evolution indicator set fulfills the predetermined location and direction criteria, thereby to produce an indication of seizure activity in the brain wave signal data.

Various other features, objects, and advantages of the invention will be made apparent to those skilled in the art from the following detailed description and accompanying drawings.

DETAILED DESCRIPTION OF THE INVENTION

Figure 1:
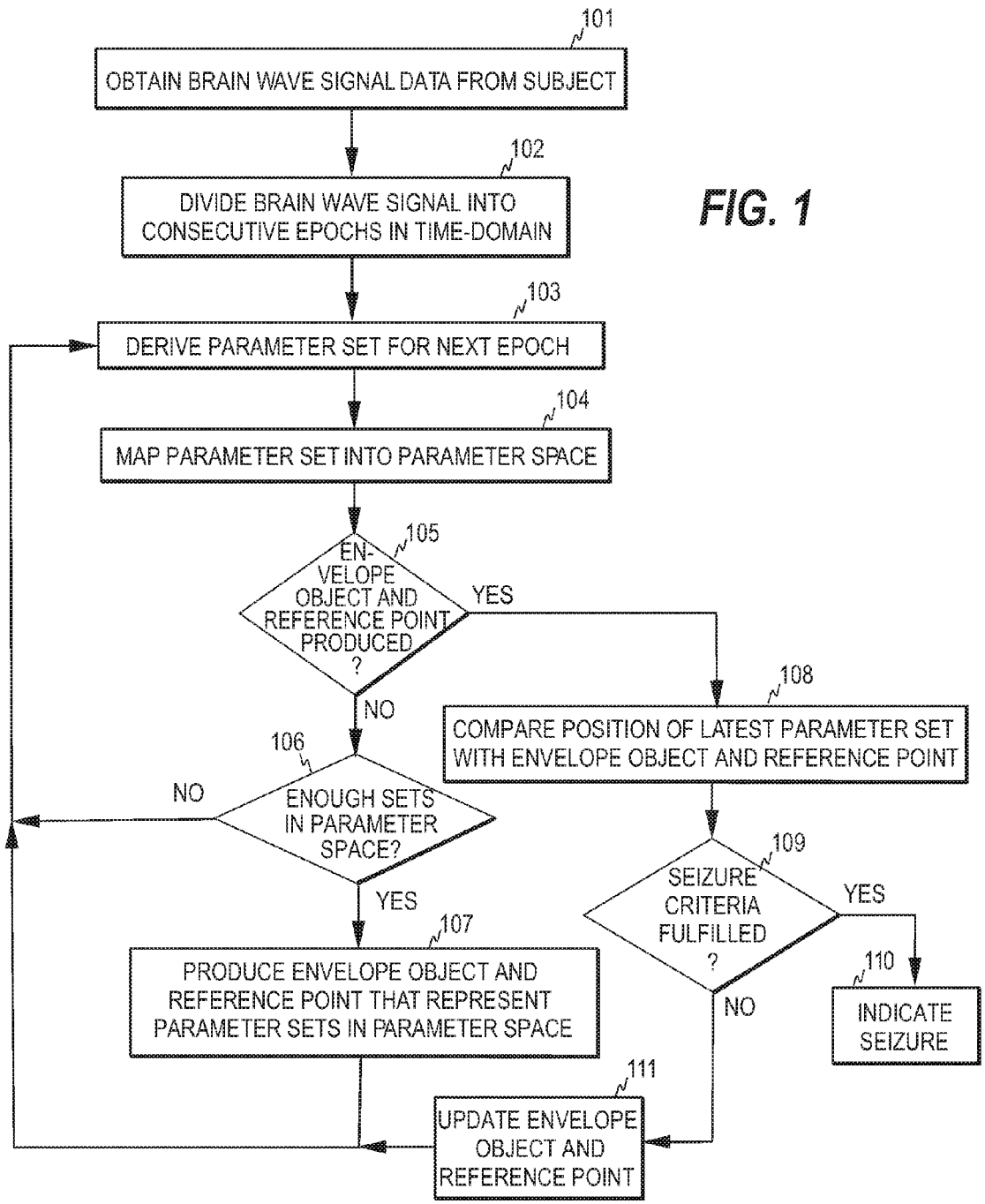
FIG. 1 is a flow diagram illustrating one embodiment of a method for monitoring seizure activity.

FIG. 1 illustrates one embodiment of a method for monitoring a brain wave signal of a subject. The operations described relate to one measurement channel and similar operations may be applied to each measurement channel if multiple measurement channels are used. Multi-channel embodiments are discussed below in connection with FIG. 5. In multi-channel embodiments, the final decision on the presence/absence of seizure activity may be made based on the multiple channel-specific decisions, for example.

As is common, the brain wave signal data obtained from the subject at step 101 is divided into consecutive time segments or time windows, commonly termed epochs (step 102). The sequence of the epochs thus represents the brain wave signal data of the respective measurement channel and the signal may be processed epoch by epoch. The length of one epoch may vary, but may be, for example, one second. The epochs may be overlapping or non-overlapping. Instead of epochs, distinct signal samples may be used to determine the parameters, although the parameters will presumably be noisier in that case.

For each epoch, a parameter set comprising at least two parameters is derived from the signal data of the epoch (step 103). That is, in step 103 the brain wave signal is parameterized, thereby to obtain respective time sequences for at least two parameters that describe the signal. For example, parameters related to the amplitude and frequency of the brain wave signal may be derived from the signal data. Alternatively, a first parameter related to the amplitude and a second parameter related to the spike rate may be derived. The determination of the parameters may include optional filtering, where the time-course of the parameters is smoothed and possible fluctuation removed. For example, median filtering of eleven sequential parameter values may be applied.

Next, the parameter values are mapped into a parameter space at step 104. The parameter space here refers to a space whose N dimensions are respectively defined by the N parameters that are determined for each epoch ($N \geq 2$). That is, the concurrent parameter values define a point in the parameter space. Typically, N equals two and the parameter space is thus a two-dimensional space, such as a plane or a coordinate system, in which one axis represents one parameter and the other axis the other parameter. When two parameters are used, the current state of the brain is represented by the point $\{x(n), y(n)\}$ in the two-dimensional parameter space, where $x(n)$ is the value of the first parameter, $y(n)$ the value of the second parameter, and n the running number of the discrete sample points in the time series. The point $\{x(n), y(n)\}$ is here termed a parameter point. That is, a parameter point is defined by the parameter set obtained for an epoch.

Next, the process examines at step 105, whether an envelope object and a reference point have already been formed and thus exist in the parameter space. If this is not the case, the process first collects enough parameter points for the generation of the envelope object (steps 103, 104, 105/no, 106/no) and generates the envelope object and the associated reference point at step 107 when it notices in step 106 that enough parameter points have been collected. The envelope object is a geometrical object that encompasses M parameter points in the parameter space, where the M parameter points are typically M latest parameter points that do not indicate seizure activity. In a case where a period of seizure activity has occurred recently, a first subset of the M parameter points may be from a period preceding the period of seizure activity and a second subset of the M parameter points from the period after the seizure activity period. Therefore, the M parameter points do not necessarily form a continuous time series of parameter points, but may form a gapped time series. The reference point is a point that depends on the M parameters points and is typically, but not necessarily, located within the envelope object. The reference point may be, for example, the center of mass of the M parameter points. The reference point may be determined directly based on the M parameter points, i.e., independently of the envelope object, but the process may also first determine the envelope object based on the M parameter points and only then the reference point based on the envelope object. For example, the reference point may be determined as the center of mass of the envelope object.

After the generation of the envelope object and the associated reference point, the process derives a new parameter set for the next epoch and maps the new parameter set into the parameter space (steps 103 and 104). The process then detects in step 105 that the envelope object and the reference point exist and jumps to step 108 for the first time. In step 108, the process compares the position of the new parameter point with the envelope object and the reference point, where the position refers to the position in the parameter space. More particularly, the position refers to the location relative to the envelope object and to the direction relative to the reference point. If the position fulfills predetermined seizure criteria, the process decides in step 109 that seizure activity is present and informs the user of the seizure, step 110. If it is detected in step 109 that the location does not fulfill the seizure criteria, the envelope object and the reference point are updated at step 111 using the new parameter set. For example, the oldest parameter point of the envelope object may be replaced by the new parameter point and the envelope object and the reference point may be updated using the new set of parameter points. The process then returns to step 103 to determine the next parameter set. Consequently, the envelope object and the associated reference point serve as location and direction reference data which the position of the newest parameter point is compared to.

It is obvious that even though FIG. 1 shows the acquisition and division of the brain wave signal as the first two steps, in online monitoring these steps are carried out continuously, and steps 103 to 111 are carried out in the above manner for each epoch obtained from step 102. The processing of the epochs may also start when a given amount of history data has been collected, so that the envelope object may be generated. However, the method may also be used offline to monitor possible seizures in brain wave data acquired previously. The monitoring may also be carried out without automatically generating a user notification informing whether seizure activity is present or not. That is, the envelope object, the reference point, and the positions of the most recent parameter sets may be presented to the user, thereby to give the user a chance to compare the positions of the latest parameter points with the envelope object and the reference point, and to make a decision on the presence/absence of seizure activity based on the comparison.

The presented method is adaptive in nature. The envelope object and the associated reference point that are updated on-line learn the normal EEG patterns encountered in each patient and are thus able to adapt to the EEG signal data encountered at any given time. The method only monitors those changes in EEG characteristics that are appreciated also in clinicians' reviews.

Figure 2:
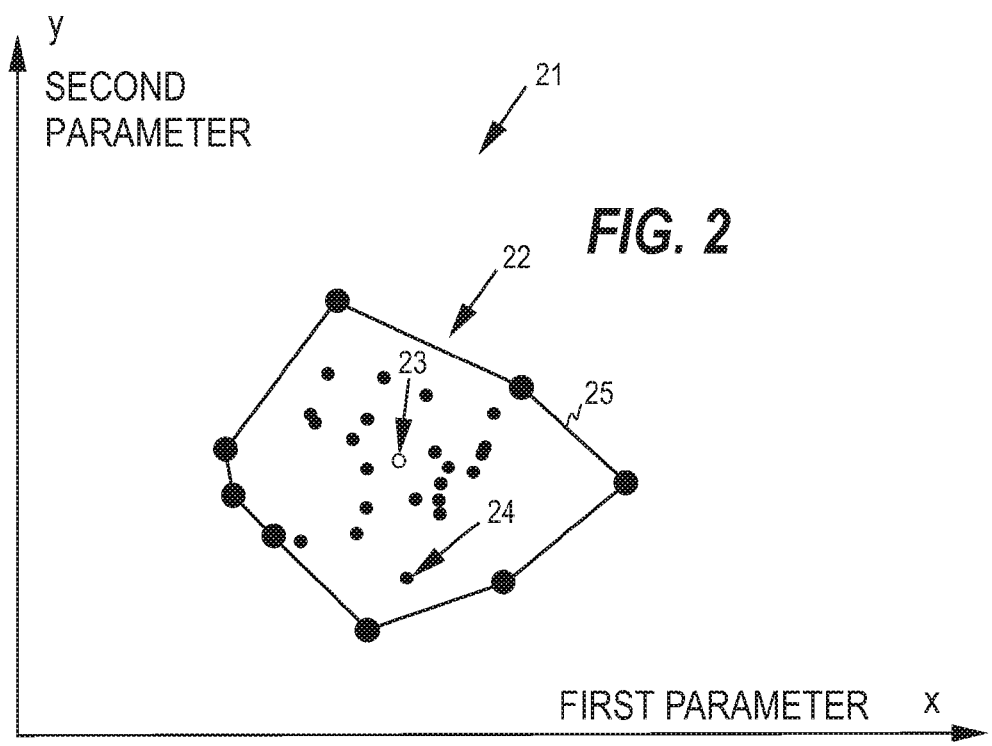
FIG. 2 illustrates an example of an envelope object in a parameter space.

FIG. 2 illustrates an example of an envelope object 22 and a reference point 23. In this example, two parameters are derived from each epoch. The parameter values obtained are then mapped into a two-dimensional parameter space 21, such as an X-Y coordinate system where the x-axis represents the first parameter and the y-axis the second parameter (or vice versa). The parameter points 24 that are mapped to the parameter space are denoted with small black dots. The envelope object is in this example a polygon 22, particularly a convex hull that encompasses the parameter points. The history lengths based on which the envelope object is formed are typically 1 to 3 minutes. Assuming that the epoch length is the above-mentioned 1 second, the envelope object is typically derived from 60 to 180 parameter points. In one embodiment, the points are the most recent parameter points that do not indicate seizure activity. Consequently, the envelope object describes how the latest seizure-free parameter points are distributed in the parameter space. Convex hull is a well-established term in mathematics and computational geometry, which relates to envelope of points located in a vector space. Several different algorithms may be used for producing a convex hull, such as the Quick Hull algorithm. One way to define the convex hull of a set X that consists of vectors $x_i$ is:

$$conv(X) = \left\{ \sum_{i=1}^{k} a_i \vec{x}_i \,\middle|\, \vec{x}_i \in X, a_i \in \mathbb{R}^+, \sum_{i=1}^{k} a_i = 1, i \in \mathbb{N} \right\}.$$

In FIG. 2, the larger black dots are the parameter points that constitute the vertices of the convex hull. The boundary 25 of the hull is defined by lines connecting the vertices. The reference point 23, which is denoted with a small circle, may be determined based on the same parameter points as the envelope object. Typically, the reference point is the center of mass of the said parameter points, but may be any point whose location depends on the parameter points and thus adapts to the parameter set time series. As mentioned above, the reference point may also be determined based on the envelope object, e.g., as the center of mass of the envelope object.

Figure 3:
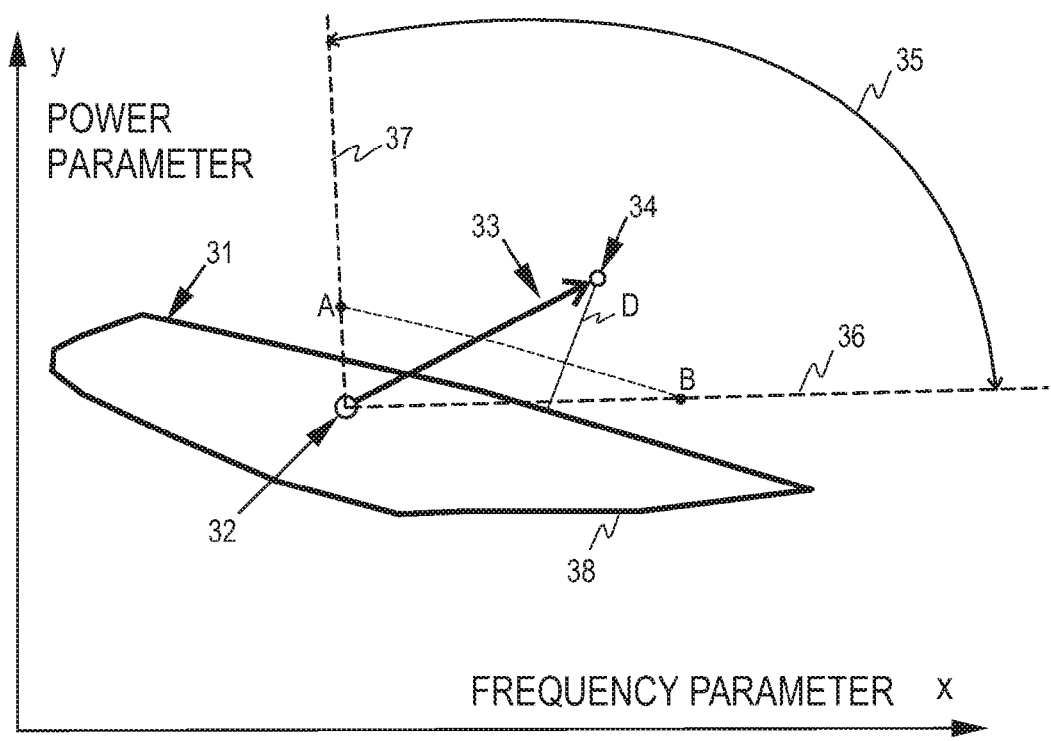
FIG. 3 illustrates an example of the seizure activity check carried out in the embodiment of FIG. 1.

FIG. 3 illustrates one embodiment of the seizure activity check carried out in steps 108 and 109 of FIG. 1. The figure shows an envelope object 31 and a reference point 32 that are formed in step 107 and updated in step 111. The parameter points have been omitted in the figure. In this embodiment, the reference point is the center of mass of the parameter points that form the envelope object. A vector 33 is then formed between the center of mass and the current parameter point 34. The vector is termed direction vector in this context, since it indicates whether the time evolution of the signal occurs towards the parameter space domain that represents seizure activity. In this example, x-axis corresponds to a frequency parameter and y-axis to a power parameter.

The seizure activity criteria set for the direction vector may vary. In one embodiment, the angle of the direction vector is to be in a predetermined sector 35 defined by a lower angle limit 36 and an upper angle limit 37 in order for the seizure activity criteria to be fulfilled, where the reference point is the apex of the sector. A further seizure criterion to be checked may be the (shortest) distance of the current parameter point from the boundary 38 of the envelope object. In FIG. 3 this distance is denoted with D. Thus, in one embodiment, the direction vector must be in a predetermined sector and the distance D must be long enough before seizure activity is detected. Apart from the envelope object and the associated reference point, the parameters that are determined for the detection of seizure activity are in this context termed evolution indicators, since they indicate whether the signal evolves to a parameter space domain considered as seizure domain. Thus, in the above embodiment the angle of the direction vector 33 and the distance D are the evolution indicators that form an evolution indicator set on which the seizure criteria are set. That is, the relative position of a parameter point must fulfill certain criteria before seizure activity is detected. Typically, the seizure criteria involve that in order for seizure activity to be detected, the position(s) of the latest parameter points must be in a predetermined sector in relation to the reference point and far enough from the boundary of the envelope object. In the example of FIG. 3 this involves that the position(s) must be in a sector area limited by the upper angle limit 37, point A, point B, and the lower angle limit 36. In a typical example, where the axes are determined by the frequency parameter and the power parameter, the sector covers a substantial majority of the first quarter, i.e., the lower angle limit is around zero and the upper angle limit around half pi in radians. As the seizure criteria are typically location and direction criteria set for the position(s) of the latest parameter point(s), the seizure criteria are also termed location and direction criteria below. The set of variables comprising the envelope object, the reference point and the evolution indicators is here termed a seizure indicator set, since the variables of the set are indicative of the presence/absence of seizure activity. The evolution indicator set may also include a feature that quantifies the length of the path made by the parameter points that are outside of the envelope object. The path here refers to the path that sequential parameter points form in the parameter space. Furthermore, the evolution indicator set may contain a signal feature that measures the amount of muscle-originated activity in the EEG signal. Seizure activity will not be indicated if a high amount of EMG is detected in the signal.

The angle criterion reduces false positive seizure detections caused by various EEG patterns, such as burst-suppression and alpha coma. Burst-suppression is an EEG pattern commonly found in ICU patients. Burst-suppression may emerge as a result of medication or it may be related to a neurological dysfunction. Epileptiform features may be present in burst-suppression patterns, but burst-suppression should not be confused with seizure activity per se. Considerable amount of changes are present in the EEG signal during burst-suppression. Small-voltage periods alternate with higher-voltage periods, where high frequencies are suppressed. In the described method, these changes are seen as simultaneous changes in the frequency parameter and in the power parameter. In the described parameter space, these changes occur in a sector other than the changes that are related to seizure activity. More specifically, burst-suppression pattern translates to changes between lower right area and upper left area of the two-dimensional parameter space. Evolution related to seizure activity occurs in a different sector of the parameter space. Hence, by applying the location and direction criteria, false positive detections resulting from burst-suppression patterns may be minimized.

Alpha coma is another problematic pattern present in ICU patients. In alpha coma, the EEG stays rather stationary as the steady alpha rhythm is the dominating component in the signal. Alpha coma is sometimes confused with seizure activity, but the alpha coma pattern should not be treated with anti-epileptic drugs. Hence, it should not trigger seizure detection. During alpha coma, there is little evolution in the described signal parameters. Even though the absolute parameter values are abnormal, the adaptive nature of the described system prevents detections resulting from alpha coma. At the onset of alpha coma, i.e., when other rhythms wane, false detections may be prevented by the evolution indicator set that quantifies the amount of evolution. Furthermore, rapid alpha burst onset is typically seen as a sudden jump in the frequency parameter values with little change in the power parameter values.

It is to be noted here that though the location of the reference point depends on the parameter points that form the envelope object and though the reference point is typically within the envelope object, the reference point may also be outside the envelope object, if, for example, the reference point is obtained by adding a fixed vector to the center of mass of the parameter points that form the envelope object.

Figure 4:
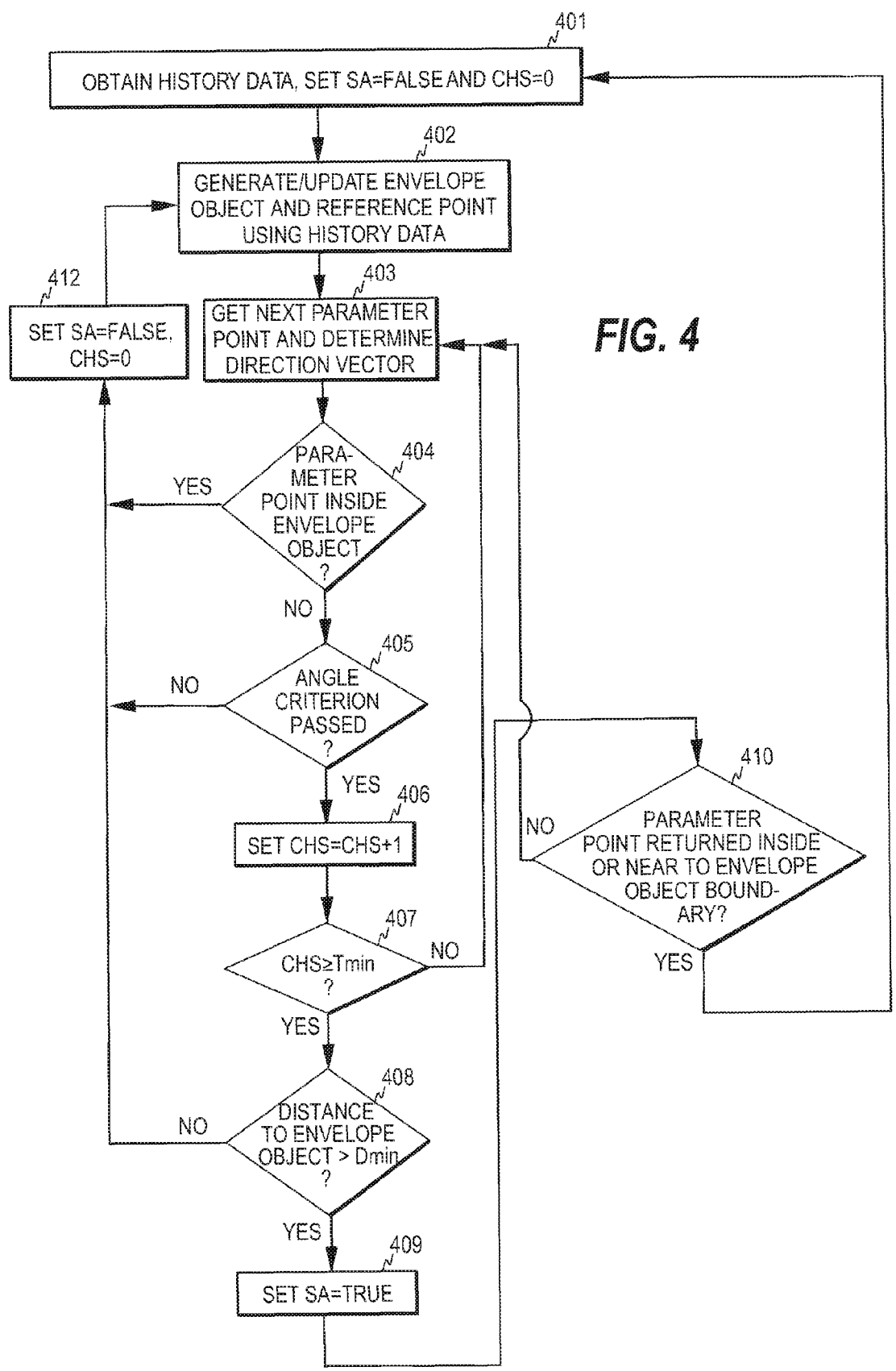
FIG. 4 illustrates a further embodiment of the method for monitoring seizure activity.

FIG. 4 illustrates another embodiment of the method for monitoring a brain wave signal of a subject. In this embodiment, four different criteria must be fulfilled before seizure activity is detected. In the example of FIG. 4, variables SA and CHS are used. SA is a Boolean variable having values "true" (seizure activity present) and "false" (no seizure activity present), and CHS is a counter that stores the number of consecutive parameters points that are outside the envelope object. The purpose of CHS is to avoid false positive detections caused by transients or other interference of very short-term duration. In this embodiment, the history data is first collected, variables SA and CHS are set to zero (step 401), and the envelope object and the reference point are produced (step 402). In the production of the envelope object and the reference point, detected past seizure events may be omitted. Upon generation of the envelope object and the reference point, the process determines the direction vector based on reference point and the current parameter point (step 403). The process then examines four different criteria in steps 404, 405, 407, and 408, respectively. In step 404, the process examines if the current parameter point is inside the envelope object. If this is not the case, the process examines in step 405 whether the angle criterion is fulfilled. If the angle criterion is met, counter value CHS is incremented (step 406) and the process then examines in step 407 whether the counter value has reached a minimum value of Tmin. If this is the case, the process further examines in step 408 whether the distance of the current parameter point to the boundary of the envelope object is greater than a required minimum Dmin. If this is the case, variable SA obtains value "true" at step 409. In other words, seizure activity is detected if the above-mentioned four different criteria are met. If it is detected in step 404 that the current parameter point is inside the envelope object or if it is detected in step 405 that angle of the direction vector is not in the predetermined sector, the process returns to step 402 via step 412 in which variable SA is set to value "false" and variable CHS to value zero. A similar transition occurs if it is detected in step 408 that the distance to the boundary is shorter than the required minimum Dmin. If it is detected in step 407 that the counter value has not yet reached a minimum value of Tmin, the process returns to step 403 to get the next parameter point and to generate the respective direction vector.

After step 409, the process checks whether the measurement may already be restored after detection of seizure activity. In this example, restoration is performed if the parameter point has returned inside or near to the boundary of the envelope object, which is tested in step 410. If this is the case, the envelope object and the reference point are re-produced and the variables are returned to their initial values as the process returns to step 401. If the restoration criterion is not fulfilled, the process returns to step 403 to get the next parameter point and to determine the associated direction vector.

In the embodiment of FIG. 4, each new parameter set is subjected to a plurality of checks before seizure activity may be detected. Certain features, such as the parameter point being inside the envelope object, immediately indicate that no seizure activity is present and thus detection of such a feature immediately stops the seizure activity detection process for the current parameter point, cf. step 404/no. As mentioned above, detection of high EMG level may be one feature that cancels detection onset. Another feature that may stop the detection process is that the length of the path outside the boundary of the envelope object is shorter than a required minimum path length, wherein the path length is a parameter indicative of the length of a path formed by successive parameter points in the parameter space. Although this path length criterion may be used instead of the above criteria requiring a minimum number of consecutive parameter points outside the envelope object (step 407), the two criteria may also be used in parallel to avoid false positive detections caused by different types of short-term interference.

Instead of, or in addition to, the criterion tested in step 410, other criteria may also be used to check whether the measurement may be restored after detection of seizure activity. Such criteria may include shortening path length (path length shortens when seizure ends), detection of post-ictal suppression that indicates the end of seizure activity, and detection of muscle convulsions.

Each evolution indicator set determined after the generation of the envelope object and the reference point may also be determined based on more than one consecutive parameter sets. This embodiment of evolution indicator set generation may also be applied to the multi-channel embodiments discussed below. The term second parameter set sequence is used below to refer to the one or more parameter sets based on which an evolution indicator set may be produced, while the term first parameter set sequence refers to the parameter sets based on which the location and direction references, i.e., the envelope object and the reference point, are determined.

The number and types of the parameters to be derived epoch by epoch may depend on the application. For seizure detection in a two-dimensional space, one suitable parameter set may comprise a first parameter indicative of a frequency and a second parameter indicative of the amplitude/power of a brain wave signal. These parameters may be estimated in various ways. Further, the seizure activity criteria typically depend on the parameters defining the parameter space.

As mentioned above, the monitoring may be carried out without a machine-generated notification of presence/absence of seizure activity. In these embodiments, the evolution indicator set, or the position(s) of the latest parameter point(s), of each parameter set time series may be presented to the user. Additionally, information may be presented to the user, which enables the user to evaluate whether or not seizure activity is present. This information may include the envelope object and/or the reference point and/or the criteria that are set for the evolution indicator set. In case of machine-generated notifications, both presence and absence notifications may be used, or the notifications may be skipped when seizure activity is not present.

As mentioned above, the parameters used may represent frequency and amplitude of the brain wave signal. The frequency of a sinusoidal signal is a well-defined quantity. However, non-stationary signals, such as EEG, do not lend themselves well to decomposition into sinusoidal components. For such signals, the notion of frequency loses its effectiveness, and a parameter that accounts for the time-varying nature of the process needs to be used. Instantaneous frequency (IF) is a time-varying parameter, which defines the location of the signal's spectral peak as it varies with time. Physically, the said parameter is meaningful for single-component signals only. For multi-component signals, the notion of a single-valued instantaneous frequency becomes physically meaningless, although it may still characterize the frequency content of the signal under analysis. To overcome this limitation, a multi-component signal may be filtered to several adjacent frequency bands and the instantaneous frequency may be estimated within each band.

Hilbert transform is a traditional method for instantaneous frequency derivation. The Hilbert transform of a signal s(t) is obtained by:

$$H[s(t)] = p.v. \int_{-\infty}^{\infty} \frac{s(t-\tau)}{\pi\tau} d\tau,$$

where p.v. denotes the Cauchy principal value of the integral and τ is the time lag. Signals s(t) and H[s(t)] are often said to be in quadrature, because in theory they are 90 degrees out of phase. However, in theory this is true only under certain conditions. Gabor's complex signal z(t) may be derived using the result of the Hilbert transform:

$$z(t)=s(t)+jH[s(t)]=a(t)e^{j\phi(t)}.$$

Using Gabor's complex signal z(t), instantaneous frequency IF may be derived by taking the derivative of the phase of signal z(t):

$$IF(t) = \frac{1}{2\pi}\frac{d}{dt}[\arg z(t)] = \frac{1}{2\pi}\frac{d\phi}{dt}$$

Mean IF value of the epoch may be used as a frequency-related parameter.

Alternatively the frequency-related parameter may be estimated by using the signal moments and/or Hjorth parameters. Even moments of the signal are determined as:

$$\overline{\omega}_m = \int_{-\pi}^{\pi} \omega^m S(e^{j\omega}) d\omega,$$

where m is even and denotes the order of the moment, and $S(e^{j\omega})$ is the power spectral density of the signal. In this context, the term signal moment is used in relation to the above equation, whereas the term spectral moment is sometimes used with the same meaning. As a person skilled in the art recognizes, the zeroth moment of a signal is the same as the total power of the signal.

Hjorth parameters or Hjorth slope descriptors have been widely used in EEG signal analysis since the 1970's. They are easy-to-calculate parameters for demonstrating the spectral properties of a signal. The first Hjorth parameter is activity. It corresponds to the zeroth moment of the same signal, i.e., to total power. The second Hjorth parameter is mobility, defined as the square root of the normalized second order signal moment:

$$\text{Mobility} = \sqrt{\frac{\overline{\omega}_2}{\overline{\omega}_0}},$$

Mobility characterizes the dominant frequency of a signal. Estimation of the dominant frequency using the mobility equation often produces a similarly looking time-curve as the IF derivation via Hilbert transform. Yet, there is still one Hjorth parameter called complexity. Complexity characterizes half the bandwidth of the signal and it is determined as:

$$\text{Complexity} = \left|\sqrt{\frac{\overline{\omega}_4}{\overline{\omega}_2} - \frac{\overline{\omega}_2}{\overline{\omega}_0}}\right|.$$

Mobility and complexity have a physically meaningful relationship to the spectral landmarks, dominant frequency and respectively half the bandwidth, only in case of a unimodal power spectrum, i.e., in case of a signal with only one dominant frequency peak. In the case of multimodal signals this limitation may be avoided similarly as already described in connection with the Hilbert transform, i.e., by using a priori filtering, for example, thereby to divide the frequency range into several sub-bands.

Although the Hjorth parameters and the even signal moments are above determined via the power spectral density of the signal, they may also be estimated directly from the time-domain EEG signal. The first derivative $x^{(1)}$ and the second derivative $x^{(2)}$ of a signal may be approximated using two and three consecutive signal samples:

$$x^{(1)}(n)=x(n)-x(n-1)$$

$$x^{(2)}(n)=x(n+1)-2x(n)+x(n-1)$$

Accordingly, estimates of the even signal moments may be determined using the following time domain average:

$$\hat{\bar{\omega}}_m \approx \frac{2\pi}{N} \sum_{n=0}^{N-1} (x^{(m/2)}(n))^2, m = 0, 2, 4\ldots$$

Various other frequency estimates may also be produced through the consecutive time domain signal samples and derivatives, thereby to produce a univariate frequency parameter. For example, energy operators, such as a non-linear energy operator (NLEO) may be applied for that purpose. Nonlinear energy operator is defined as:

$$\Psi_{NLEO}\{x(n)\}=x(n-l)x(n-p)-x(n-q)x(n-s),$$

where the index values are selected so that l+p=q+s, and |l−q|=|p−s|≠0. The index values may be selected, for example as follows: l=1, p=2, q=0, and s=3. In EEG applications, the absolute value of NLEO is often preferred. The nonlinear energy operator, as defined above, is not a pure measure of frequency, since the changing signal amplitude affects it as well. To obtain a rough estimate of the signal frequency, the nonlinear energy operator may be divided by $x(n)^2$.

The number of times the signal changes sign during each epoch is a simple feature corresponding roughly to the dominant frequency of the signal. However, the main problem with the use of the feature as a frequency parameter is the sensitivity to noise. The rate of the zero crossings may, on the other hand, be used as a measure of the noisiness of the signal in some applications. Similarly as with the Hilbert transform and Hjorth parameters, a priori filtering may make the rate of the zero crossings less susceptible to noise.

Spectral edge frequencies denote the limit frequencies of the sub-bands containing given percentiles of the total power of the signal. For example, median frequency or 50% spectral edge frequency (SEF50%) denotes the limit frequency, which cuts the total power into two halves: 50% of the power resides below the SEF50% frequency and 50% above. Other commonly used SEF parameters are SEF90% and SEF95%, which indicate that 90% (or 95%) of the power of the signal is below the frequency concerned. Peak power frequency indicates the frequency with the highest power peak in the power spectral density. The mean frequency of the EEG may be calculated using the following equation:

$$MeanFreq = \frac{\sum_i f(i)S(i)}{\sum_i S(i)}$$

It should be noted that odd signal moments cannot be calculated using the power spectral density S, since it is an even function. Therefore, the numerator of the above equation is not the first moment of the signal. The odd moments of a signal may be derived from the power spectral density of Gabor's complex signal.

As described above, various techniques may be used to obtain a single parameter indicative of the current frequency content of the brain wave signal. The above frequency related parameters represent examples of the parameters that may be used as a frequency related parameter of the parameter set. However, any technique that produces a single parameter indicative of the frequency content of the brain wave signal data may be used in the parameterization phase of the signal.

The zeroth moment of the signal, i.e., the total power, is one alternative for the amplitude related parameter. As presented in the above equations, the total power may be derived either from power spectral density or directly from the time-domain signal. Another commonly used amplitude estimate is the root-mean-square (RMS) amplitude:

$$A_{RMS} = \sqrt{\frac{1}{N} \sum_{n=0}^{N-1} x(n)^2}.$$

Mean amplitude may be calculated as the average of the absolute signal sample values:

$$A_{mean} = \frac{1}{N} \sum_{n=0}^{N-1} |x(n)|.$$

Similarly, median amplitude may be derived from the absolute signal sample values. For peak-to-peak amplitude estimation, local minima and maxima are first searched for from the time-domain signal. After that, the differences of consecutive minima and maxima may be derived and used for the amplitude estimation. RMS, mean, and median peak-to-peak amplitudes may be derived similarly as described above, but by replacing the signal sample values with the difference values.

Various wave-decomposition methods have also been successfully employed in EEG signal analysis. These methods belong to the group of mimetic methods, since they often aim to mimic a human observer. In wave-decomposition methods, local minima and maxima may also be searched for, but more advanced logic and processing is often employed than in the simple peak-to-peak amplitude methods. Wave-decomposition methods may be fine-tuned to search for some predefined EEG patterns, such as EEG spikes. Using the output data of wave-decomposition, such as so-called half-waves, various amplitude and frequency estimates may be derived.

As in case of the frequency parameter, any appropriate technique may be used in the parameterization phase of the brain wave signal to produce a single parameter indicative of the current amplitude of the brain wave signal.

As discussed above, filtering prior to the generation of the parameters may lead to improved signal-to-noise ratio. Often, band-pass filtering improves the sensitivity and specificity of the parameters to track the EEG signal changes characteristic to seizure activity. EEG manifestations of seizure activity may be divided roughly into two categories; in the first category a significant amount of evolution takes place in the frequency and amplitude of the EEG within a short time period (from about 10 seconds to about 10 minutes), while in the second category spike activity consisting of periodical EEG spikes or sharp waves with a high repetition rate, typically at least three complexes per second, takes place. Frequency and amplitude evolution is often best visible in frequencies below about 20 Hz, whereas spike activity is best recognized in frequencies above 20 Hz. By proper selection of the cut-off frequencies of the pre-filtering stage, the method may be made more sensitive and specific to the seizure activity of interest.

When EEG is measured from the scalp of an adult, the EEG frequency range covers frequencies from 0 Hz to about 70 Hz. For monitoring evolutionary seizures, it is advantageous to remove at least part of the beta activity (13-30 Hz) and the entire gamma activity (30-70 Hz) of the EEG, thereby to improve the sensitivity and specificity of an automated seizure detector. Thus, a suitable cut-off frequency of a low-pass filter is between 12 and 20 Hz. Further, low frequencies may contain movement artifacts or other transients, or low-frequency fluctuation caused by perspiration or poor electrode contacts. Therefore, it is advantageous to use high-pass filtering with the cut-off frequency being somewhere between or around 1 and 2 Hz. After applying the above-described filters, the output data still contains the most relevant signal components characteristic to evolutionary seizures. As discussed above, the filtering may be carried out before the parameterization of the brain wave signal, and it may also be carried out before the division of the signal into consecutive epochs, i.e., before step 102 of FIG. 1 and before step 51 of FIG. 5 below.

The parameter space may also be expanded to dimensions higher than two, although the presentation and interpretation may become more complicated as the dimension of the parameter space increases. In case of a three-dimensional space, the third parameter may be, for example, spike rate, which defines how many spikes are detected in a predefined time window.

In one embodiment, the two-dimensional parameter space may be adaptive, i.e., the y-axis may represent one parameter, such as amplitude/power, but the parameter represented by the x-axis may vary. For example, x-axis may represent either instantaneous frequency or spike rate, depending on the type of seizure activity. Spike rate is a preferred parameter in case of detected spike activity, whereas instantaneous frequency is a preferred parameter for evolutionary seizures. However, many seizures are mixtures of these two categories. In other words, they have characteristics from both categories. Therefore, the process may determine a plurality of parameters from the signal data and monitor the evolution of each parameter. If a particular parameter shows significant evolution, one of the dimensions of the parameter space may be set to represent the said parameter. This may be applied to more than one parameter/dimension.

In embodiments comprising multiple signal channels temporal coherences of the parameters between the channels may also be examined. When a seizure takes place, the brain wave signals of different brain areas start to behave in a different manner, i.e., the seizure has a different effect in different brain areas. This is distinguishable especially when a partial seizure occurs.

Figure 5:
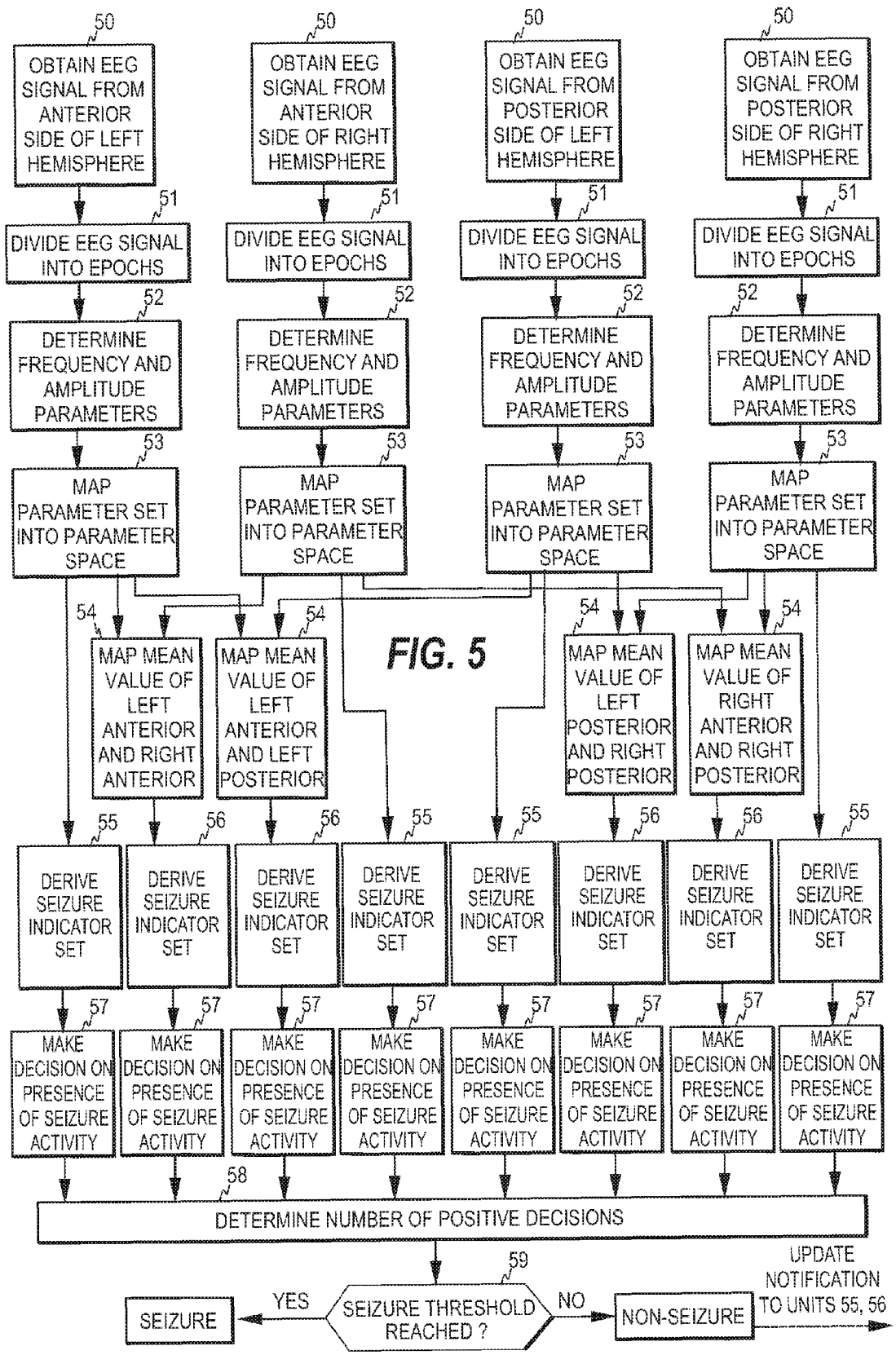
FIG. 5 illustrates an example of seizure activity detection in case of four different EEG measurement channels.

FIG. 5 illustrates one possible embodiment of a multichannel monitoring mechanism. In this example, four-channel EEG signal data is acquired from the subject at steps 50; two channels from the left hemisphere and two channels from the right hemisphere. Two EEG signals are thus obtained from each hemisphere; the measurement site of the first one of the two EEG signals is closer to the frontal brain area, while the measurement site of the second one is farther from the frontal brain area, but closer to the occipital brain area. Furthermore, the measurement site of one of the said two signals may be closer to the temporal brain area than that of the other signal. In this way, all three dimensions of the brain may be utilized: cranial-caudal, anterior-posterior, and medial-lateral. It is advantageous that the electrodes are positioned in identical positions contra-laterally, i.e., that each electrode of the left hemisphere has a pair on the corresponding brain area of the right hemisphere. The signal of each channel is again divided into consecutive epochs (steps 51).

In the example of FIG. 5, two parameters are determined for each epoch of each channel; one indicative of the amplitude and the other indicative of the frequency of the respective signal (steps 52). The parameters of each channel are then mapped to the parameter space at steps 53 (since the same parameters are determined on each channel, it is assumed here that the parameter space is common for all channels). In addition to the four channel-specific parameter sets (each comprising the said two parameters), mean parameter sets {amplitude, frequency} between the channels of the same hemisphere and between the corresponding channels of opposite hemispheres are derived and mapped into the parameter space (steps 54). Consequently, four additional parameter sets are obtained for each epoch, each additional set comprising a mean value of the amplitude parameter and a mean value of the frequency parameter.

As a result, four channel-specific parameter sets and four additional parameter sets are obtained and thus totally eight envelope objects with dedicated reference points may be derived from the four EEG signal channels obtained from the subject; four channel-specific envelope objects with respective reference points determined in steps 55 based on channel-specific parameters and four additional envelope objects with respective additional reference points determined in steps 56 based on inter-channel mean values of the parameters. The evolution indicators, such as the direction vector angle and distance D, may also be determined in steps 55 and 56. Each step 55 and 56 thus outputs, for each epoch, a seizure indicator set, i.e., an envelope object provided with a reference point and an evolution indicator set. The seizure indicator sets derived from the data of two or more different channels are here termed additional seizure indicator sets, while "seizure indicators" may refer to channel-specific seizure indicators or to additional seizure indicators. Based on each of the eight seizure indicator sets and the location and direction criteria, a decision on the presence/absence of seizure activity may then be made in steps 57, similarly as in the embodiment of FIG. 4, for example. Each step 57 thus outputs a true or false value for "seizure activity present" (variable SA) for each epoch. In step 58, the total number of simultaneous true values is determined.

When seizure activity is detected, it is detectable on one or more of the EEG signal channels. That is, for the detection of a seizure it is enough to be able to detect the seizure on one of the EEG channels, since a seizure may occur locally in the brain. If a seizure is detectable only on one of the above four channels, three seizure indicator sets are still affected: the indicator set derived from the EEG channel where the seizure is detectable and the two other indicator sets that are affected by the said EEG channel. A seizure-induced effect can thus be present in three seizure indicator sets: in the indicator set derived from the said EEG channel and in the two additional indicator sets on which the said channel affects. Thus, the seizure threshold used in step 59 may be one, two or three. That is, in one embodiment seizure is detected if it is detected in step 59 that at least one of the eight simultaneous decisions is indicative of seizure activity, in another embodiment seizure is detected if it is detected in step 59 that at least two of the eight simultaneous decisions are indicative of seizure activity, and in a further embodiment seizure is detected if it is detected in step 59 that at least three of the eight simultaneous decisions are indicative of seizure activity. If seizure activity is not detected at step 59, the history data is updated to obtain updated envelope objects and reference points for the next epoch.

It is also possible that a probability measure is calculated based on each seizure indicator set to obtain eight probability measures, each measure being indicative of the estimated probability of seizure activity on the respective parameter set time series. In this embodiment, the operations carried out in steps 57 to 59 differ from those of the above embodiment in which eight simultaneous decisions are made in step 57. Instead of making the above-described eight time-series-specific decisions, the eight probability measures may be calculated in step 57. As a seizure affects three indicator sets, the process may then determine, for example, the mean of three largest probability measures in step 58. In step 59, the mean may then be compared with a respective seizure threshold value, thereby to decide on the presence/absence of seizure activity. As above, the history data is updated if seizure activity is not detected, thereby to obtain updated envelope objects and reference points for the next epoch.

Compared to the single-channel embodiment of FIG. 1, the multi-channel embodiment of FIG. 5 offers improved perceptivity in seizure detection, since it is more efficient in detecting seizures confined to a limited area of the brain. In other multi-channel embodiments, it may not be necessary to use all channels for seizure activity detection, but the method may be applied to a subset of channels. Moreover, it may not be necessary to employ inter-channel parameter values, but only channel-specific seizure indicators sets may be used. However, depending on the application it may also be possible that all seizure indicator sets are additional indicator sets formed based on the brain wave data of two or more channels. if additional seizure indicator sets are determined based on one or more channel pairs or other channel combinations, the number of such additional indicator sets may vary. Furthermore, another aggregate value than the mean may be determined based on a channel pair or channel combination.

The parameters derived epoch by epoch from the EEG data may also be provided with predefined weighting factors. The usage of different weights for the parameters may improve the sensitivity and specificity of the seizure detection.

Figure 6:
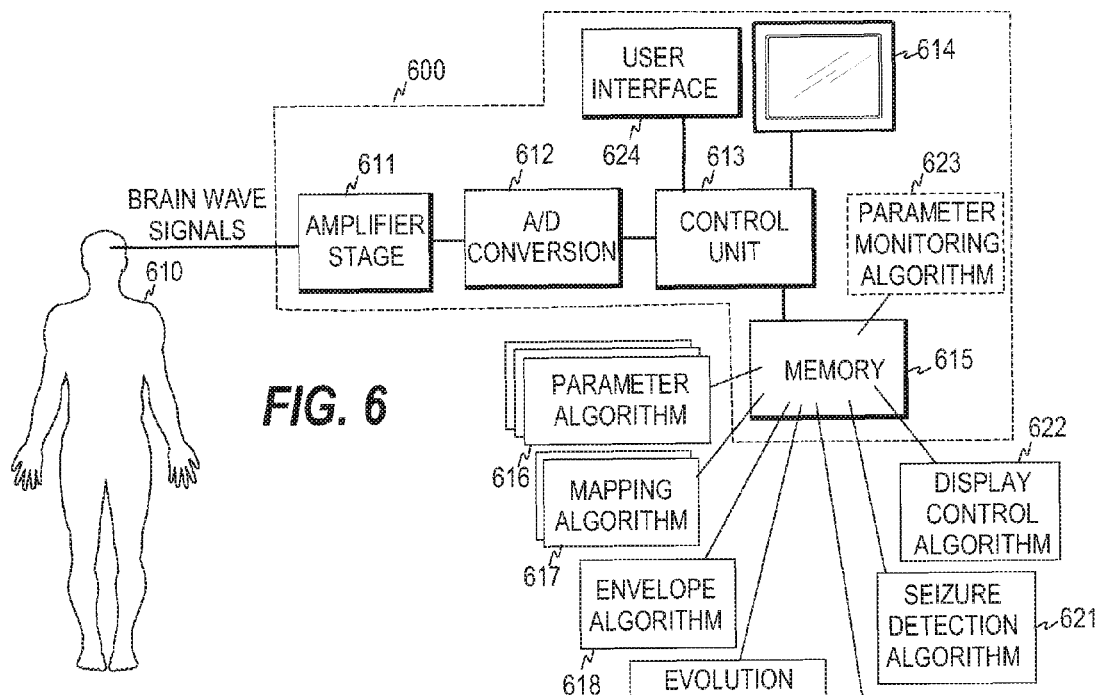
FIG. 6 illustrates an apparatus/system for monitoring seizure activity based on one or more brain wave channel signals.

FIG. 6 illustrates one embodiment of the apparatus or system for monitoring seizure activity. The brain wave data acquired from a subject/patient 610 is typically EEG signal data. In the case of a single or dual channel EEG measurement, the forehead of the patient is a preferred EEG measurement site due to the ease of use of the measurement and the reduced inconvenience caused to the patient. However, various electrode placement systems may be used, especially in multi-channel embodiments. One possible placement system is described in connection with FIG. 5.

The signals obtained from the EEG sensors are supplied to an amplifier stage 611, which amplifies the signals before they are sampled and converted into digitized format in an A/D converter 612. The digitized signals are then supplied to a control and processing unit 613 (including a microprocessor), which may then record the signals as an EEG time series and divide the signals into consecutive epochs.

The control and processing unit is provided with a memory or database unit 615 holding the digitized EEG signal data obtained from the sensors. Before the actual evaluation of the signal data, the control and processing unit may perform various pre-processing phases for improving the quality of the EEG signal data or the said phases may be carried out in separate elements located between the EEG sensors and the control and processing unit. The actual recording of the EEG signal data thus occurs in a conventional manner, i.e., the measurement device 600 including the above elements serves as a conventional EEG measurement device.

Additionally, the control and processing unit 613 is provided with executable algorithms for monitoring seizure activity in the EEG channel data. For determining the parameters epoch by epoch for each channel, the control and processing unit may use one or more parameter determination algorithms 616 to derive the parameters from the signal data. The control and processing unit may further use one or more mapping algorithms 617 to map the parameter values into the parameter space, thereby to obtain at least one parameter point time series in the parameter space, and an envelope algorithm 618 configured to determine the envelope object and the respective reference point in the parameter space for each time series. To generate the evolution indicator sets, the control and processing unit may execute algorithm 619 adapted to determine the evolution indicators. For the comparison of the evolution indicators with the location and direction criteria, a separate comparison algorithm 620 may be provided. The control and processing unit may further be provided with a seizure detection algorithm 621 configured to make a decision on the presence of a seizure, when executed by the control and processing unit, and with a display control algorithm 622 configured to present monitoring results to the user. The control and processing unit may display the results on the screen of a monitor 614 connected to the control and processing unit. This may be carried out in many ways using textual and/or graphical information about the monitoring and/or seizure detection results. The information may be accompanied by visual and/or audible alarms, when seizure activity is detected. The seizure detection algorithm 621 may initiate the update of the history data if seizure activity is not detected for current epoch, so that the envelope algorithm 618 is constantly able to use the latest history data for the determination of the envelope objects and reference points.

If an adaptive parameter space is used, the control and processing unit may also be provided with a parameter monitoring algorithm 623, which, when executed by the control and processing unit, selects the parameters that define the parameter space.

The system further includes a user interface 624 through which the user may control the operation of the system.

Figure 7:
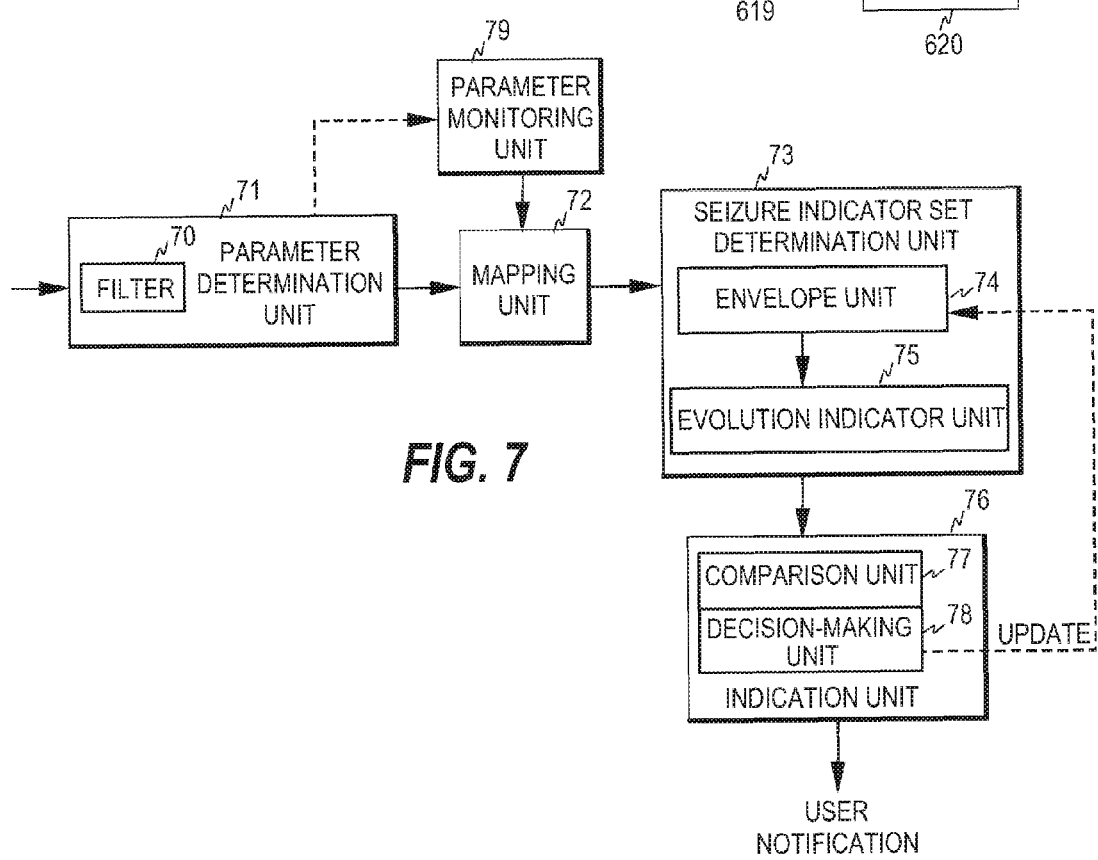
FIG. 7 illustrates the operational entities of the control and processing unit of the apparatus/system of FIG. 6.

As shown in FIG. 7, in terms of monitoring seizure activity the control and processing unit may thus include multiple operational entities: a parameter determination unit 71 configured to derive at least two parameters from each epoch of each channel used for the monitoring, a mapping unit 72 configured to map the parameters obtained from unit 71 to the parameter space, and a seizure indicator set determination unit 73 configured to determine the envelope object, the associated reference point, and the evolution indicators for each time series. Unit 73 may thus be divided into separate subunits; an envelope unit 74 configured to determine and update the reference data obtained based on the history data, i.e. the envelope object and the reference point, and an evolution indicator unit 75 configured to determine the evolution indicators based on the latest parameter point(s). The parameter determination unit 71 may be provided with a pre-filter 70 for removing gamma activity and part of the beta activity prior to the parameterization of the brain wave signal data.

The seizure indicator sets of each time series may be supplied as input data to an indication unit 76 configured to employ the input information, thereby to give an indication of seizure activity to the user. The indication unit may include comparison and decision-making units 77, 78 configured respectively to compare the evolution indicator sets with the predetermined location and direction criteria and to make decisions on the presence of seizure activity. The decision-making unit may control the update of history data in the envelope unit, depending on whether or not seizure activity is detected. However, the decision-making unit may also carry out the update for the envelope unit. The operations needed for the update are included in units 77, 78, and 74, and therefore the said units may be regarded as an update unit that conditionally updates the history data and the envelope objects and the reference points. If an adaptive parameter space is used, the control and processing unit may further include a parameter monitoring unit 79 configured to select the parameters that define the parameter space.

It is to be noted that FIGS. 6 and 7 illustrate the division of the functionalities of the control and processing unit in logical sense and in view of evaluation of signal evolution. In a real apparatus the functionalities may be distributed in different ways between the elements or units of the apparatus. For example, the mapping functions and functions for determining the seizure indicator sets may be included in the same unit. Moreover, each unit may carry out its operations for one or more channels/time series and the parameter unit may determine parameter aggregate values, such as mean values, for one or more channel pairs or channel combinations. Further, the functionalities depend on the embodiment. For example, the functionalities may differ considerably depending on whether or not a machine-generated notification of presence/absence of seizure activity is implemented.

Furthermore, though one control and processing unit (data processing entity) may perform the calculations needed, the processing of the brain wave signal data may be distributed among different data processing entities within a distributed system or network, such as a hospital LAN (local area network). For example, a conventional measurement device may record the EEG signal data and an external computing entity, such as processor or server, may be responsible for seizure monitoring.

The brain wave signal data may be EEG signal data or magnetoencephalographic (MEG) signal data. MEG is indicative of the magnetic component of brain activity, i.e., it is the magnetic counterpart of EEG. The measurement device 600 may thus also serve as a conventional MEG measurement device, although a MEG measuring arrangement is far more expensive than an EEG measuring arrangement.

The software enabling a conventional EEG or MEG measurement device 600 to monitor/detect seizure waveforms may also be delivered separately to the measurement device, for example on a data carrier, such as a CD or a memory card, or through a telecommunications network. In other words, a conventional EEG or MEG measurement device may be upgraded by a plug-in unit that includes software enabling the measurement device to evaluate signal evolution and possibly also to detect seizures in the above-described manner. The software module may comprise algorithms 617 to 620 and 622, and possibly also algorithm 621, although the content of algorithm 621 may depend on the implementation of the user view. To maintain updated history data, the comparison functionality of algorithm 620 is needed for deciding when to update the history data. The software may also be used to analyze brain wave signal data offline. Should the conventional measurement device determine the parameters needed for the determination of the seizure indicators, it may be possible to omit the parameter algorithm(s) 616 from the software module. The software portion configured to derive the parameter set sequence(s) from the brain wave signal data may also include the above-described pre-filter configured to remove gamma activity and at least part of beta activity from the brain wave signal data prior to derivation of the parameter set sequence(s). The software plug-in unit may utilize a dedicated display unit for monitoring seizure activity.

Above, one method for producing the envelope object geometrically is described. Alternatively, the envelope object may be produced analytically. As examples of analytical envelope object creation some principles are presented below. First, the object may be described analytically in the parameter space. These implementations include computing statistical variables from the parameter set distribution and defining a closed curve based on those variables. To give an example, the parameter sets may be orthogonalized and an ellipse (in 2-D parameter space) or an ellipsoid (in 3-D parameter space) may be defined that describes the distribution. For example, the semiaxes may be defined by directions that maximize variance (PCA—Principal Component Analysis): Let D represent the matrix of past centered parameter points, with rows being the parameter points. Apply singular value decomposition to obtain $D=WSV^T$, where W contains the singular vectors of D, or, equivalently, eigenvectors of covariances of parameter points that can be used, together with diagonal values of S to define the said closed curves. In PCA, directions of the semiaxes are defined by the criterion of maximizing variance. A further example is to use ICA (Independent Component Analysis) that implements the criterion of maximizing statistical independence of variables. A yet further example would be to define the range of each parameter value and define a rectangle (in 2-D parameter space) or a rectangular cuboid (in 3-D parameter space) that encloses the parameter sets or a subset of the parameter sets. Second, the envelope object may be described by the parameter sets. An example is the convex hull described above. The hull may be defined as a list of parameter sets.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for monitoring seizure activity in brain, the method comprising:
   deriving a first parameter set sequence in a parameter determination unit from brain wave signal data obtained from a subject, wherein the first parameter set sequence comprises sequential parameter sets and each parameter set comprises values for at least two signal parameters, the values being derived from the brain wave signal data;
   determining an envelope object in an envelope unit from the first parameter set sequence in a parameter space defined by the at least two signal parameters, wherein the envelope object encompasses the first parameter set sequence in the parameter space;
   determining a reference point, wherein location of the reference point in the parameter space depends on the first parameter set sequence;
   obtaining a second parameter set sequence in the parameter determination unit from the brain wave signal data, wherein the second parameter set sequence comprises at least one parameter set subsequent to the sequential parameter sets of the first parameter set sequence;

determining an evolution indicator set in an evolution indicator unit that is indicative of (a) location of the second parameter set sequence in relation to the envelope object and (b) direction of the second parameter set sequence in relation to the reference point;

conditionally updating the envelope object and the reference point based on (i) sequential parameter sets of the first parameter set sequence and (ii) the second parameter set sequence, wherein the conditionally updating comprises performing the updating if the evolution indicator set fails to fulfill predetermined location and direction criteria indicative of seizure activity and skipping the updating if the evolution indicator set fulfills the predetermined location and direction criteria; and indicating whether the evolution indicator set fulfills the predetermined location and direction criteria, thereby to produce an indication of seizure activity in the brain wave signal data.

2. The method according to claim 1, further comprising acquiring the brain wave signal data from the subject.

3. The method according to claim 2, wherein:
the acquiring includes acquiring a plurality of brain wave signal channels from the subject, in which each brain wave Channel contains the brain wave signal data
the deriving includes deriving the first parameter set sequence for each of the plurality of brain wave signal channels, thereby to obtain a corresponding plurality of first parameter set sequences;
the determining of the envelope object includes determining the envelope object from each Of the corresponding plurality of first parameter set sequences, thereby to obtain a corresponding plurality of envelope objects;
the determining of the reference point includes determining the reference point for each of the corresponding plurality of first parameter set sequences, thereby to obtain a corresponding plurality of reference points;
the obtaining includes obtaining the second parameter set sequence for each of the plurality of brain wave signal channels, thereby to obtain a corresponding plurality of second parameter set sequences;
the determining of the evolution indicator set includes determining an evolution indicator set for each of the corresponding plurality of the second parameter set sequences, thereby to obtain a corresponding plurality of evolution indicator sets;
the conditionally updating includes comparing each of the corresponding plurality of evolution indicator sets with the predetermined location and direction criteria, thereby to obtain a corresponding plurality of comparison results; and
the indicating includes producing the indication of seizure activity based on the corresponding plurality of comparison results.

4. The method according to claim 1, wherein the deriving and obtaining include determining the values of the at least two signal parameters, in which the at least two signal parameters comprise a first signal parameter indicative of instantaneous frequency of the brain wave signal data and a second signal parameter indicative of power of the brain wave signal data.

5. The method according to claim 4, wherein:
the determining of the evolution indicator set includes determining the evolution indicator set in the parameter space, wherein dimensions of the parameter space are determined by the first signal parameter and the second signal parameter; and the conditionally updating includes examining whether the second parameter set sequence is outside the envelope object and within a sector in the parameter space, wherein the reference point constitutes an apex of the sector.

6. The method according to claim 4, wherein:
the denying further comprises deriving at least one additional first parameter set sequence, wherein each of the at least one additional first parameter set sequence comprises sequential parameter sets and each parameter set comprises aggregate values for the at least two similar parameters, each aggregate value being derived from a given set of brain wave signal channels;
the determining of the envelope object further comprises determining an envelope object for each of the at least one additional first parameter set sequence, thereby to obtain at least one additional envelope object;
the determining of the reference point further comprises determining a reference point for each of the at least one additional first parameter set sequence, thereby to obtain at least one additional reference point;
the determining of the evolution indicator set further includes determining an additional evolution indicator set for each of the at least one additional envelope object, thereby to obtain at least one additional evolution indicator set;
the conditionally updating includes comparing each of the at least one additional evolution indicator set with the predetermined location and direction criteria, thereby to obtain at least one additional comparison result; and
the indicating includes producing the indication of seizure activity based on the corresponding plurality of comparison results and the at least one additional comparison result.

7. The method according to claim 1, wherein the determining of the envelope object includes determining the envelope object geometrically by a convex hull algorithm.

8. The method according to claim 1, wherein the indicating includes indicating whether the evolution indicator set fulfills the predetermined location and direction criteria, in which the indicating is performed at least when the updating is skipped, thereby to produce the indication of seizure activity at least when the evolution indicator set fulfills the predetermined location and direction criteria.

9. The method according to claim 8, wherein the indicating includes indicating presence of seizure activity when the updating is skipped and indicating absence of seizure activity when the updating is performed.

10. An apparatus for monitoring seizure activity in brain, the apparatus comprising:
a parameter determination unit configured to derive a first parameter set sequence from brain wave signal data obtained from a subject, wherein the first parameter set sequence comprises sequential parameter sets and each parameter set comprises values for at least two signal parameters, the values being derived from the brain wave signal data;
an envelope unit configured to determine (i) an envelope object from the first parameter set sequence in a parameter space defined by the at least two signal parameters and (ii) a reference point, wherein the envelope object encompasses the first parameter set sequence in the parameter space and wherein location of the reference point in the parameter space depends on the first parameter set sequence;
an evolution indicator unit configured to define an evolution indicator set indicative of (a) location of the second parameter set sequence in relation to the envelope object and (b) direction of the second parameter set sequence in relation to the reference point, wherein the parameter determination unit is configured to derive the second parameter set sequence and wherein the second parameter set sequence comprises at least one parameter set subsequent to the sequential parameter sets of the first parameter set sequence;

an update unit configured to conditionally perform an update of the envelope object and the reference point based on (i) sequential parameter sets of the first parameter set sequence and (ii) the second parameter set sequence, wherein the update unit is configured to perform the update if the evolution indicator set fails to fulfill predetermined location and direction criteria indicative of seizure activity and skip the update if the evolution indicator set fulfills the predetermined location and direction criteria; and an indication unit configured to indicate whether the evolution indicator set fulfills the predetermined location and direction criteria, thereby to produce an indication of seizure activity in the brain wave signal data.

11. The apparatus according to claim 10, further comprising a measurement unit configured to acquire the brain wave signal data from the subject.

12. The apparatus according to claim 11, wherein:
the measurement unit is configured to acquire a plurality of brain wave signal channels from the subject, in which each brain wave channel contains the brain wave signal data
the parameter determination unit is configured to derive the first parameter set sequence for each of the plurality of brain wave signal channels, thereby to obtain a corresponding plurality of first parameter set sequences;
the envelope unit is configured (a) to determine the envelope object for each of the corresponding plurality of first parameter set sequences, thereby to obtain a corresponding plurality of envelope objects and (b) to determine the reference point for each of the corresponding plurality of first parameter set sequences, thereby to obtain a corresponding plurality of reference points;
the parameter determination unit is configured to obtain the second parameter set sequence for each of the plurality of brain wave signal channels, thereby to obtain a corresponding plurality of second parameter set sequences;
the evolution indicator unit is configured to determine an evolution indicator set for each of the corresponding plurality of second parameter set sequences, thereby to obtain a corresponding plurality of evolution indicator sets;
the update unit is configured to compare each of the corresponding plurality of evolution indicator sets with the predetermined location and direction criteria, thereby to obtain a corresponding plurality of comparison results; and
the indication unit is configured to produce the indication of seizure activity based on the corresponding plurality of comparison results.

13. The apparatus according to claim 10, wherein the at least two signal parameters comprise a first signal parameter indicative of instantaneous frequency of the brain wave signal data and a second signal parameter indicative of power of the brain wave signal data.

14. The apparatus according to claim 13, wherein:
dimensions of the parameter space are determined by the first signal parameter and the second signal parameter; and the update unit is configured to examine whether the second parameter set sequence is outside the envelope object and within a sector in the parameter space, wherein the reference point constitutes an apex of the sector.

15. The apparatus according to claim 13, wherein:
the parameter determination unit is further configured to derive at least one additional first parameter set sequence, wherein each of the at least one additional first parameter set sequence comprises sequential parameter sets and each parameter set comprises aggregate values for the at least two signal parameters, each aggregate value being derived from a given set of brain wave signal channels;
the envelope unit is further configured to determine an envelope object for each of the at least one additional first parameter set sequence, thereby to obtain at least one additional envelope object and to determine a reference point for each of the at least one additional first parameter set sequence, thereby to obtain at least one additional reference point;
the evolution indicator unit is further configured to determine an additional evolution indicator set for each of the at least one additional envelope object, thereby to obtain at least one additional evolution indicator set;
the update unit is configured to compare each of the at least one additional evolution indicator set with the predetermined location and direction criteria, thereby to obtain at least one additional comparison result; and
the indication unit is further configured to produce the indication of seizure activity based on the corresponding plurality of comparison results and the at least one additional comparison result.

16. The apparatus according to claim 10, wherein the envelope unit is configured To determine the envelope object geometrically by a convex hull algorithm.

17. The apparatus according to claim 10, wherein the indication unit is configured to produce the indication of seizure activity at least when the evolution indicator set fulfills the predetermined location and direction criteria.

18. The apparatus according to claim 17, wherein the indication unit is configured to indicate presence of seizure activity when the update is skipped and to indicate absence of seizure activity when the update is performed.

19. A non-transitory computer program product for monitoring seizure activity in brain, the computer program product comprising:
a first program product portion configured to derive a first parameter set sequence from brain wave signal data obtained from a subject, wherein the first parameter set sequence comprises sequential parameter sets and each parameter set comprises values for at least two signal parameters, the values being derived from the brain wave signal data:
a second program product portion configured to determine (i) an envelope object from the first parameter set sequence in a parameter space defined by the at least two signal parameters and (ii) a reference point, wherein the envelope object encompasses the first parameter set sequence in the parameter space and wherein location of the reference point in the parameter space depends on the first parameter set sequence:,
a third program product portion configured to define an evolution indicator set indicative of (a) location of the second parameter set sequence: in relation to the envelope object and (b) direction of the second parameter set sequence in relation to the reference point, wherein the first program product portion is configured to derive the second parameter set sequence and wherein the second parameter set sequence comprises at least one parameter set subsequent to the sequential parameter sets of the first parameter set sequence;

a fourth program product portion configured to conditionally perform an update of the envelope object and the reference point based on the (1) sequential parameter sets of the first parameter set sequence and (ii) the second parameter set sequence, wherein the fourth program product portion is configured to perform the update if the evolution indicator set thus to fulfill predetermined location and direction criteria indicative of seizure activity and skip the update if the evolution indicator set fulfills the predetermined location and direction criteria; and a fifth program product portion configured to indicate whether the evolution indicator set fulfills the predetermined location and direction criteria, thereby to produce an indication of seizure activity in the brain wave signal data.

20. The program product according to claim 19, wherein:

the fourth program product portion is configured to compare the evolution indicator set with the predetermined criteria, thereby to obtain a comparison result, and to make a decision on presence of seizure activity based on the comparison result; and the fifth program product is configured to indicate the decision to a user.

* * * * *